United States Patent [19]
Kweon et al.

[11] Patent Number: 6,107,396
[45] Date of Patent: Aug. 22, 2000

[54] METHOD OF PREPARING A COMPOSITE OF ORGANIC AND INORGANIC COMPOUNDS

[75] Inventors: Ho-jin Kweon; Sung-soo Kim, both of Choongcheongnam-do; Dong-gon Park, Seoul; Jin Kang, Seoul; Hye-young Kwon, Seoul, all of Rep. of Korea

[73] Assignee: Samsung Display Devices Co., Ltd., Suwon-si, Rep. of Korea

[21] Appl. No.: 09/192,864

[22] Filed: Nov. 16, 1998

[30] Foreign Application Priority Data

Feb. 5, 1998 [KR] Rep. of Korea .......................... 98-3274

[51] Int. Cl.[7] ....................................................... C08J 5/05
[52] U.S. Cl. ........................... 524/779; 524/783; 526/210; 526/227; 526/229; 526/319; 526/329.7
[58] Field of Search ..................................... 524/779, 783; 526/227, 229, 319, 329.7, 210

[56] References Cited

U.S. PATENT DOCUMENTS 5,019,293  5/1991  Burlitch ................................ 252/313.1
5,153,031  10/1992  Burlitch ................................ 427/226

*Primary Examiner*—Robert Dawson
*Assistant Examiner*—Jeffrey B. Robertson
*Attorney, Agent, or Firm*—Christie, Parker & Hale, LLP

[57] ABSTRACT

A method of preparing a composite of organic and inorganic compounds includes the steps of reacting a mixed solution of a metal alkoxide and a silicon-containing compound with a catalyst to produce an alcogel of a metal oxide or a complex metal oxide. The metal alkoxide is prepared by reacting at least one metal with an alcohol and the mixed solution is prepared by mixing the metal alkoxide with the silicon-containing compound. An alcogel is produced from the reacting step and alcohol is impregnated within the inorganic oxide lattice structure of the alcogel. Furthermore, the method of preparing a composite of an organic and an inorganic compound includes the steps of centrifuging the alcogel to separate any alcohol from the alcogel to form a gel, adding an organic monomer the gel and polymerizing the organic monomer in-situ to form an organic polymer. The resulting composite has characteristics of both the parent organic and inorganic compounds.

14 Claims, 4 Drawing Sheets

METHOD OF PREPARING A COMPOSITE OF ORGANIC AND INORGANIC COMPOUNDS

CROSS REFERENCE TO RELATED APPLICATION

This application claims priority of Korean Patent Application No. 98-3274, filed Feb. 5, 1998, the content of which is incorporated hereinto by reference.

FIELD OF THE INVENTION

The present invention relates to a method of preparing a composite of organic and inorganic compounds, and more particularly, to a method of preparing a composite of an organic and an inorganic compound having characteristics of both the parent organic and inorganic compounds by combining organic and inorganic compounds which do not chemically react with each other.

BACKGROUND OF THE INVENTION

Sol-gel processing is a widely known method for the chemical synthesis of inorganic oxide compounds, including metal oxides and complex metal oxides. The sol-gel process is based on a theory that components in a solution are uniformly distributed. Generally, in the process, a metal alkoxide compound as a reactant is dissolved in an alcoholic solvent. The solution is then hydrolyzed by the addition of water and condensed to thereby obtain a sol-phase where particles are uniformly dispersed. Thereafter, the sol-phase is allowed to stand to obtain a gel-phase. When the reaction conditions are appropriately controlled, the resulting product may be endowed with a particle size ranging from several tens to several hundreds of nanometers. The gel-phase product has a three-dimensional metal oxide lattice structure where the particles of the inorganic components are chemically crosslinked with each other.

The sol-gel process has a number of advantages in that various types of products such as lenses, thin films, bulk particles and fibers can be prepared by the inorganic polymerization. However, the sol-gel process has serious limitations that do not easily allow its application to a practical use. For instance, it is difficult to obtain a desired shape from the sol-gel process because shrinkage, fracture or some form of distortion may easily occur during the process. Moreover, the final product has poor mechanical strength, causing mechanical failure of the shape (i.e. breakage) and poor solvent resistance, further resulting in denaturation of the shape. In particular, mechanical processing steps such as grinding, cutting and casting cannot be performed on the product due to its weak structure. Therefore, the sol-gel process is generally employed only for the purpose of producing precursors to crystalline powders upon heat-treatment. It is not suitable for producing amorphous products for optical purposes. More specifically, these defects are found to be more abundant in materials having at least two compositions except for silica ($SiO_2$) so that it is practically impossible to fabricate a useful optical lens by the sol-gel process. Accordingly, desirable mechanical characteristics required for such an optical lens are often obtained from processing the polymers of organic compounds rather than by sol-gel processing the inorganic compounds.

In an exemplary organic polymerization method, a peroxide as an initiator is added to methyl methacrylate (MMA) as a monomer to facilitate polymerization between double bonds of the monomer, affording organic polymers of chain type, polymethylmethacrylate (PMMA). MMA is in liquid phase at ambient temperature under ambient pressure so that it acts both as a monomer as well as a solvent for polymerization. In addition, the organic polymer is usually a homopolymer consisting of only one material so long as the polymer is not synthesized by copolymerization. Thus, it is difficult to add a guest material to the organic polymer and to control the mechanical characteristics of the organic polymer. In particular, when ions having optical characteristics or macromolecules are added to the organic polymer, only a portion of the structure of the organic polymer adjacent to the guest material is restrictively modified while other surrounding portions of the polymer structure remain unchanged.

Such defects may be overcome by producing new materials with characteristics of both the parent inorganic and organic compounds and research on producing composites of this type has been actively pursued. The composites prepared from hybrid gels composed of organic and inorganic compounds including complex components of organic and inorganic polymers are referred to as an ORMOCER or a CFRAMER.

Generally, the composite is prepared by chemically reacting inorganic portions with the organic portions and reforming the inorganic components in situ. First, an alkoxide functional group of the metal alkoxide being a reactant in the inorganic polymerization step is partially substituted with organic monomers. Thereafter, the inorganic portions react with the organic portions via the substituted functional group.

Alternatively, research has been conducted to produce composites of organic and inorganic compounds without the aforementioned chemical treatment. An alcogel from the sol-gel process is first dried for a long time to obtain a dried gel and, then, an organic monomer is impregnated into the rigid metal oxide lattice of the dried gel to facilitate organic polymerization therein. In this process, the term alcogel refers to a gel that is impregnated with alcohol. However, the method using the alcogel has certain limitations in that the alcogel should be dried for several months so as to obtain a useful gel. Furthermore, the yield of the gel is extremely low.

In order to avoid such disadvantages while reducing the drying time, a crucial drying step is employed accompanying the sol-gel process to produce composites of organic and inorganic compounds in a relatively short time. However, it is known that the method cannot be applied to organic polymers such as PMMA which can not chemically bond to the inorganic oxide lattice.

Moreover, an investigation been made to combine an organic polymer with an inorganic oxide lattice structure. However, because the polymer is composed of long chains, it is not easy to produce the type of composites described herein.

SUMMARY OF THE INVENTION

The present invention is concerned with a method of preparing a composite of an organic compound and an inorganic compound without the drying step while increasing the yield of the composite.

In addition, the present invention provides a method of preparing a composite of an organic compound and an inorganic compound by a simple process without reforming a reactant, that is, without requiring a chemical reaction between the functional groups of the organic and the inorganic compounds and, more particularly, by incorporating organic polymers, such as PMMA, which do not chemically react with the inorganic compounds.

Another aspect of the present invention provides a method of preparing a composite of an organic and an inorganic compound for preventing light diffusion due to the large size of the inorganic oxide particles formed, by controlling the particle size to be on the order of several tens of nanometers, and controlling the optical characteristics of functional ions or macromolecules added as guest materials.

Yet another aspect of the present invention provides a method of preparing a composite of an organic and an inorganic compound having characteristics of both the parent organic and inorganic compounds while insuring improved optical transmittance and transparency sufficient for a lens application.

To accomplish these aspects, the method of preparing a composite of an organic compound and an inorganic compound includes the step of preparing a metal alkoxide by reacting at least one metal with an alcohol. The metal alkoxide is mixed with a silicon-containing compound to form a solution. The next step involves reacting the mixed solution of the metal alkoxide and the silicon containing compound with a catalyst to produce an alcogel of a metal oxide or a complex metal oxide, the resulting alcogel having an inorganic oxide lattice structure. In the alcogel produced from the reacting step, alcohol is impregnated into the inorganic lattice structure.

Furthermore, the method of preparing a composite of an organic compound and an inorganic compound includes the steps of centrifuging the alcogel to separate any alcohol from the alcogel to form a gel, adding an organic monomer to the gel, polymerizing the organic monomer to form an organic polymer containing the inorganic lattice structure of the gel and permitting the organic polymer to harden, thereby forming the composite.

BRIEF DESCRIPTION OF THE DRAWINGS

The accompanying drawings, which are incorporated in and constitute a part of the specification and, together with the description, serve to more clearly explain the principles of the invention, wherein.

DETAILED DESCRIPTION OF THE INVENTION

Figure 1:
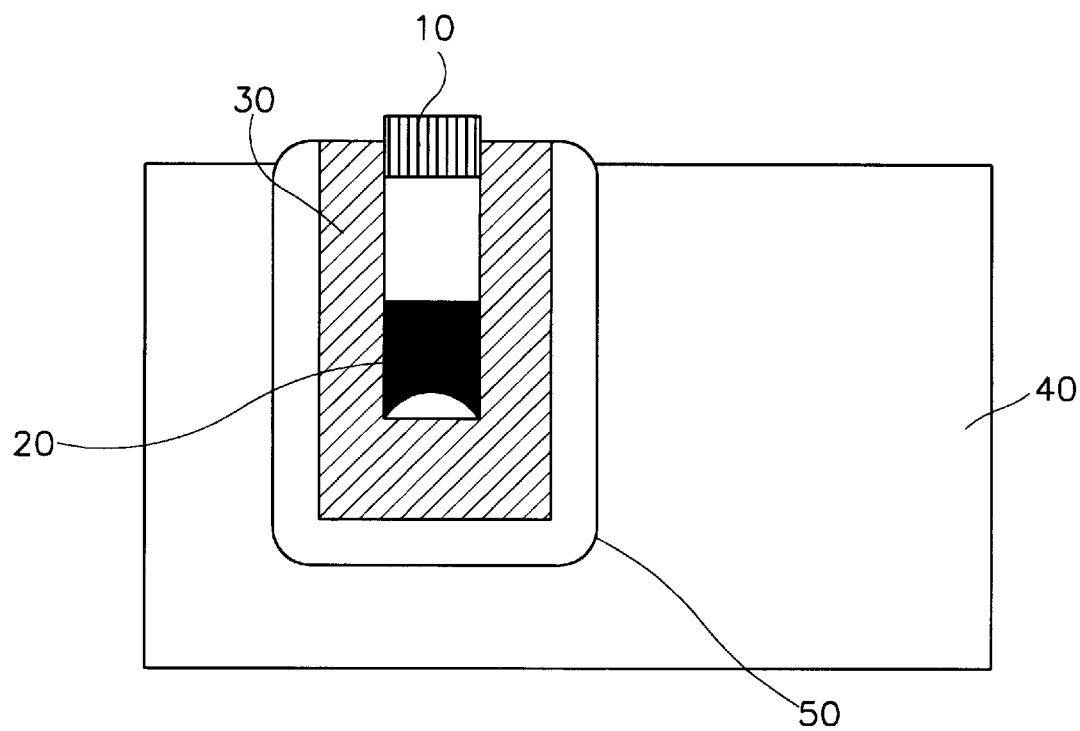
FIG. 1 is a partial sectional view showing a centrifuge for producing the composite of the present invention.

The present invention provides a method of preparing a composite of an organic compound and an inorganic compound. In the method, an alcohol is reacted with at least one metal to produce a metal alkoxide, and the metal alkoxide is then mixed with a silicon-containing compound. The mixture in the presence of a catalyst produces an alcogel. In the produced alcogel, alcohol is impregnated into the alcogel and within the inorganic oxide lattice of the alcogel. The alcogel is centrifuged to separate any alcohol from the inorganic oxide lattice to form a gel. Thereafter, an organic monomer is added to the gel containing the inorganic lattice structure and polymerized to form an organic polymer. The organic polymer is permitted to harden, thereby forming the composite. The method of preparing a composite of an organic and an inorganic compound will now be illustrated in more detail.

The resulting composite of an organic compound and an inorganic compound requires an oxide lattice or particle size of several tens of nanometers to provide excellent optical transmittance. In order to prepare such a composite, a sol-gel reaction is performed by using a compound selected from hydrogen peroxide (30%, $H_2O_2$), or peroxides of magnesium, sodium and lithium as a catalyst to prepare a gel precursor consisting of complex metal oxide.

In preparing the gel precursor, a metal such as magnesium, sodium or lithium, reacts with an alcohol such as methanol in a predetermined amount to form a metal alkoxide. A silicon-containing compound such as a silicon alkoxide selected from tetraethylorthosilicate (TEOS) and tetramethylorthosilicate (TMOS) is then mixed with the metal alkoxide. Thereafter, a peroxide, such as hydrogen peroxide, as a catalyst and distilled water are slowly added to the mixed solution. When the peroxide is added, the mixed solution undergoes a sol-gel reaction to form the gel precursor of a metal oxide. The metal is most preferably magnesium (Mg). When Mg is used as the metal, forsterite ($Mg_2SiO_4$) or enstatite ($MgSiO_3$) may be formed as the gel precursor.

Alcohol is impregnated throughout the gel precursor, and the gel impregnated with alcohol is generally called an "alcogel". The metal used as a reactant with the alcohol is very sensitive to hydrolysis. Therefore, when aqueous acid or base used in the conventional sol-gel process is directly used as a catalyst, unstable gels may be obtained. However, in the present method, when a peroxide such as hydrogen peroxide is used as the catalyst, a very stable alcogel having inorganic oxide particles with diameters on the order of several tens of nanometers may be obtained. The particle size of the alcogel may be evaluated by measuring the transmittance of the alcogel in the visible wavelength region. Namely, when the transmittance of the alcogel is similar to that of air in the visible range, this indicates the particle size of the prepared alcogel is below several tens nanometers.

When the alcogel prepared by using peroxide as the catalyst is dried to remove the alcoholic solvent from the alcogel and within the oxide lattice structure thereof, problems such as shrinkage, fracture and certain distortions of the alcogel occurs during the drying step. Moreover, nanometer-sized particles get entangled with one another forming aggregates, thus enlarging the overall size of the particles from a magnitude of micrometers to millimeters so that such particles lose their optical transmittance.

In order to avoid such problems, the alcohol is separated from the alcogel and the inorganic lattice structure of the alcogel by centrifuging it to form a gel. An organic monomer is then added to the gel in order to form an organic polymer around the gel and within the oxide lattice structure of the gel. The organic monomer may be at least one monomer selected from monomers having polymerizable double bonds, such as MMA (methyl methacrylate), or MA (methacrylate). The organic monomer is preferably MMA. In order to completely replace any remaining alcohol with the organic monomer, it is preferable that the centrifuging and monomer-adding steps are repeated. The monomer is then polymerized by adding benzylperoxide as an initiator and allowing the organic polymer to harden, thereby producing a composite of an organic compound and an inorganic compound without requiring the drying step.

As the organic polymerization proceeds, a composite body without chemically bonding the inorganic and organic compounds may be prepared. A nano composite of an inorganic polymer and an organic polymer such as PMMA with neither polymer forming any chemical bonds with the other can be prepared. The solvent substitution and polymerization steps are performed preferably in the centrifuging bath in order to prevent the occurrence of bubbles and the fracture of the inorganic lattice structure caused by transferring the gel from a reaction vessel of the centrifuge to a new reaction vessel.

The composite of an organic compound and an inorganic compound prepared by the above method has a structure essentially composed of entangled organic polymer chains within and around the inorganic oxide lattice such that the nanometer-sized characteristics of the inorganic oxide lattice are maintained and the composite body has the desired optical transmittance. The composite body has most of its volume occupied by the organic polymer constituents with relatively small quantities of the inorganic oxide constituents. Generally, the weight ratio of the inorganic constituents to the total composite ranges from about 4 to 8%. When a lens is prepared by cutting the composite to a predetermined size and heated to burn away the organic portion, a body consisting of only inorganic constituents with its own shape may be obtained. Accordingly, it is observed that the inorganic oxide lattice structure is uniformly distributed over the composite.

As described above, the inorganic constituents of the oxide lattice structure uniformly distributed over the composite serve to significantly modify certain optical characteristics of the added optical functional guest material without lowering the optical transmittance of the composite. The functional guest material may be added to the composite by adding a compound including the functional guest material to the mixed solution for preparing the alcogel. For instance, when a composite is prepared by using the metal alkoxide mixed with $Eu(NO_3)_3 5H_2O$, $Eu^{3+}$ ions are uniformly distributed over the composite. The phosphor, $Eu^{3+}$ ion, is the guest material which provides the desired optical characteristics to the nano composite.

According to this method, the emission spectrum exhibited by $Eu^{3+}$ ions incorporated in the composite has certain optical characteristics which depend on the inorganic oxide lattice structure rather than the organic polymer. The functional guest material is not limited to the preferred phosphor and includes all materials capable of forming a composite by uniformly combining with the alcogel in the mixing step.

Because the oxide lattice structure is distributed over the composite even in relatively small quantities, the composite has complex mechanical characteristics that are a hybrid of both the organic and inorganic constituents. In other words, the composite has excellent mechanical characteristics as compared to composites of inorganic oxides prepared in the sol-gel process. Furthermore, it is relatively easy to mechanically cast, grind or cut the composite, and the composite has excellent resistance to solvents. Moreover, the composite has better thermal characteristics as compared to composites containing only organic compounds.

The present invention is further explained in more detail with reference to the following examples. The examples are not intended to limit the present invention.

EXAMPLE 1

Magnesium corresponding to an amount in the mole ratio of twice more than silicon in TEOS (tetraethylorthosilicate) was reacted with dry methanol to afford $Mg(OMe)_2$. $Mg(OMe)_2$ was then mixed with TEOS to prepare a mixed solution.

Hydrogen peroxide and the twice distilled water corresponding to an amount in the mole ratio of four times more than silicon in TEOS were weighed and diluted with methanol, respectively.

Each of the diluted solutions were slowly added to the mixed solution of TEOS and $Mg(OMe)_2$ to undergo a sol-gel reaction of the magnesium oxide and the silicon oxide constituents therein to form an alcogel of fosterite ($Mg_2SiO_4$), an inorganic oxide. The formed alcogel was endowed with a high transmittance in the visible range, and it was determined that the particle size of fosterite in the alcogel was on the order of several tens of nanometers.

The alcogel was allowed to stand at ambient temperature for a predetermined time to strengthen the inorganic lattice structure therein. The initial alcogel forming process and this standing step were all carried out under an inert gas atmosphere. The alcogel allowed to stand for a predetermined time was exposed to the air, and equal volumes of a base and toluene were added thereto. The mixture was allowed to stir for a predetermined time to further strengthen the inorganic lattice structure.

Thereafter, as shown in FIG. 1, the alcogel 20 was transferred into a reaction vessel 10 of a centrifuge and centrifuged at a rate of 2000 rpm for 2 hours to separate the alcohol from the inorganic oxide lattice. In the centrifuge shown in FIG. 1, reference numerals 30, 40 and 50 denote an adapter, a centrifuge rotor and a centrifuge housing, respectively.

The separated alcohol was decanted and a monomer (MMA) was added to the alcogel to replace any alcohol with MMA. The aforementioned separating, decanting and addition steps refer to a washing step. The washing step was repeatedly carried out to increase the concentration of MMA so that any remaining alcohol is essentially substituted with MMA. During the final washing step, a predetermined amount of benzylperoxide as a polymerization initiator for MMA was added to the gel.

When the gel, where the alcohol solvent was substituted with MMA, was heat-treated in an oven heated at 45° C. without transferring the gel from the reaction vessel, MMA distributed within the inorganic oxide lattice of the gel was subsequently polymerized to form organic polymer chains of PMMA around and within the inorganic lattice structure.

In the process, since the reaction vessel 10 employed in the solvent substituting step was used again in the polymerization step, the step of transferring the gel from the reaction vessel 10 to a new reaction vessel may be omitted and any disruption or fracture of the oxide lattice structure and/or the occurrence of bubbles in the gel may be prevented. The polymerization reaction lasted from one day to several days. When the polymerization reaction was completed, a hard and optically transparent composite was produced.

A nano composite of an organic compound and an inorganic compound of fosterite and PMMA obtained by polymerizing the organic monomer around and within the inorganic oxide lattice of the gel in-situ were either cut or ground to make a product of a predetermined shape.

Figure 2:
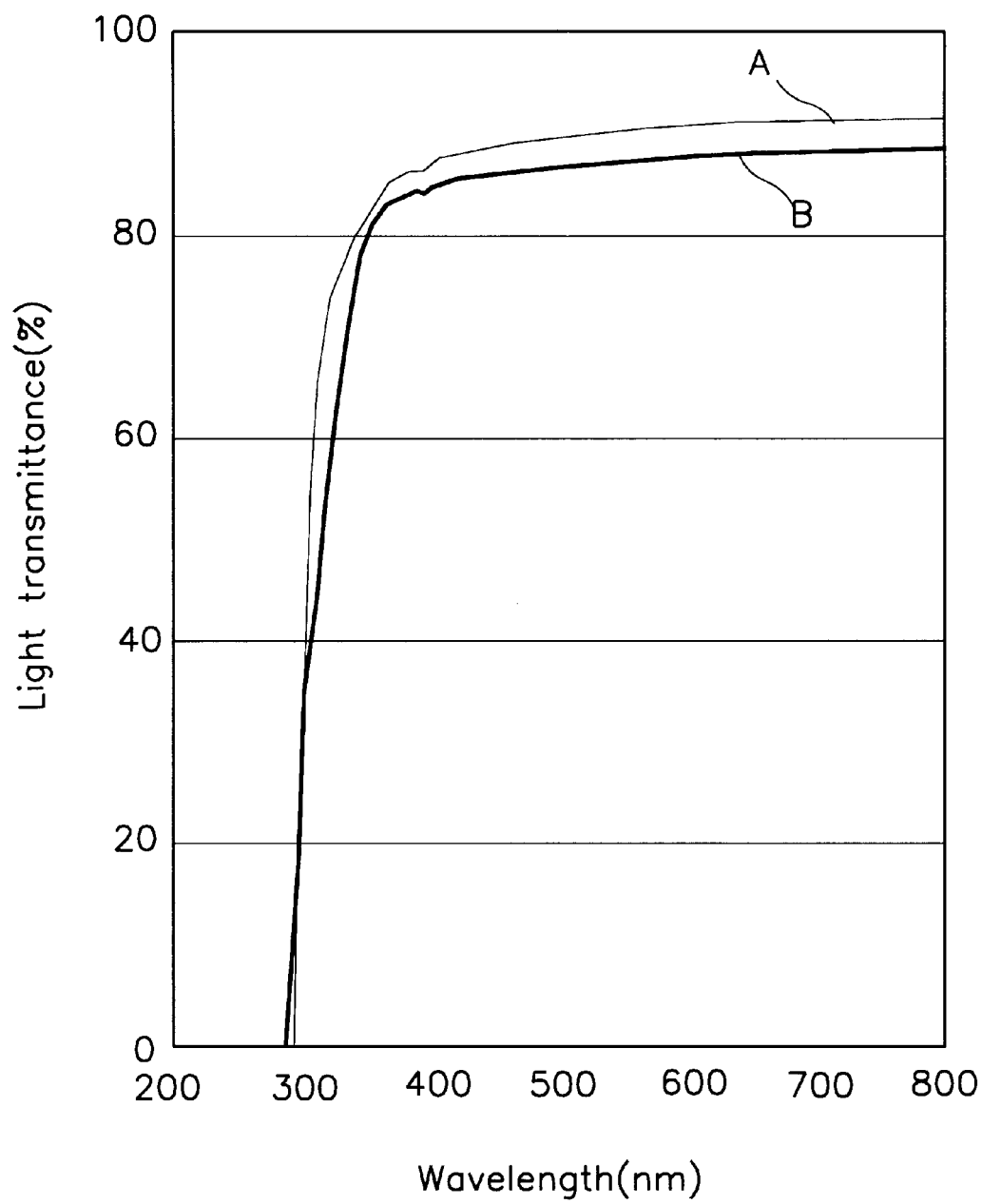
FIG. 2 is a graph illustrating the light transmittance as a function of wavelength for a composite according to the present invention and pure PMMA in the ultraviolet-visible region.

FIG. 2 shows an ultraviolet-visible spectrum of the transmittance of a lens body produced by cutting and grinding the nano composite of fosterite-PMMA. As shown in FIG. 2, the transmittance of the composite of Example 1 (curve B) is about 88% the transmittance of the air (determined to be 100%). Furthermore, it is almost identical to the transmittance of a pure PMMA body. That is, when compared with a spectrum of the pure PMMA body having the same size, the transmittance of the composite of Example 1 (curve A) is about 98%. As a result, it turns out that the inorganic oxide lattice structure of the inventive composite has no substantial effect on the transmittance of the inventive composite.

The mechanical and thermal characteristics of the composite of fosterite-PMMA, a dried gel incorporating only fosterite, and a homopolymer of pure PMMA were evaluated, and the results are summarized in Table 1.

TABLE 1

| SAMPLE | SURFACE HARDNESS [Kg/mm$^2$] | FRACTURE TOUGHNESS [MPa] | Tg [° C.] | Tm [° C.] |
|---|---|---|---|---|
| PMMA homopolymer | 2.66 | >>200 | 100 | 200 |
| Forsterite-PMMA composite | 5.0 | 140 | 120 | 250 |
| Forsterite gel | 33.0 | <<1 | — | — |

As shown in Table 1, the surface hardness of the composite is similar to PMMA, whereas the fracture toughness thereof is substantially higher than the dried forsterite gel but smaller than PMMA, which exhibits high elasticity. In other words, the composite of the present invention has characteristics of both the parent organic and inorganic compounds. Furthermore, due to the inorganic oxide constituents, the Tg (Glass transition temperature) of the composite increased about 20° C. compared to pure PMMA and Tm (melting temperature) increased about 50° C. compared to pure PMMA.

Example 2

Magnesium corresponding to an amount in the mole ratio of twice more than silicon in TEOS was reacted with dry methanol to afford $Mg(OMe)_2$. The $Mg(OMe)_2$ was then mixed with TEOS, and $Eu(NO_3)_2 \cdot 5H_2O$ corresponding to an amount in the mole ratio of 0.05 times more than silicon was added thereto to produce a mixed solution. The $Eu(NO_3)_2 \cdot 5H_2O$ is a guest material for giving the desired optical characteristics to the inventive composite. Thereafter, hydrogen peroxide and twice distilled water corresponding to an amount in the mole ratio of four times more than silicon in TEOS were weighed and diluted with methanol, respectively.

Each of the diluted solutions were slowly added to the mixed solution of TEOS and $Mg(OMe)_2$ to undergo a sol-gel reaction of magnesium oxide and silicon oxide to form an alcogel of fosterite ($Mg_2SiO_4$) containing $Eu^{3+}$ ions. The formed alcogel incorporating $Eu^{3+}$ ions was allowed to stand at ambient temperature for a predetermined time to strengthen and further condense the metal oxide components of the inorganic lattice structure therein. The initial alcogel forming process and this standing step were all carried out under an inert gas atmosphere.

The alcogel allowed to stand for a predetermined time was exposed to the air, and equal volumes of a base and toluene were added thereto and allowed to stand for a predetermined time to further strengthen. Thereafter, as shown in FIG. 1, the alcogel 20 was transferred to a reaction vessel 10 of a centrifuge and centrifuged at the rate of 2000 rpm for 2 hours to separate any alcohol from the alcogel.

The separated alcohol was decanted, and MMA as an organic monomer was added to the gel to replace any alcohol with MMA. The aforementioned separating, decanting and addition steps refer to a washing step. The washing step was repeatedly carried out to increase the concentration of MMA in the gel so that any remaining alcohol is essentially substituted with MMA. During the final washing step, a predetermined amount of benzylperoxide as a polymerization initiator for MMA was added to the gel. When the gel, where the alcohol solvent was substituted with MMA, was heat-treated in an oven heated at 45° C., MMA distributed within the inorganic oxide lattice structure of the gel was subsequently polymerized to form organic polymer chains of PMMA around and within the inorganic lattice structure.

A composite of an organic compound and an inorganic compound of fosterite and PMMA which incorporated $Eu^{3+}$ ions was obtained by polymerizing the organic monomer around and within the inorganic oxide lattice of the gel in-situ, then was cut or ground to make a product having a predetermined shape.

Figure 3A:
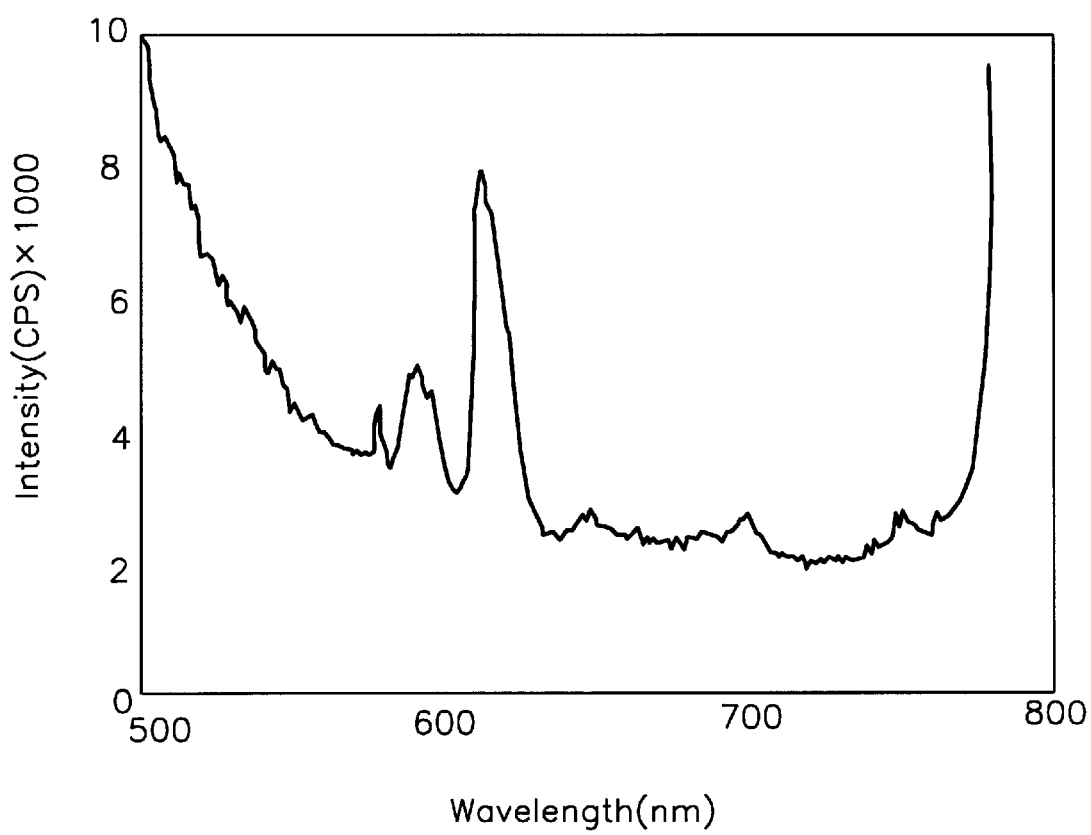
FIG. 3a is a luminescence-emission spectrum as a function of wavelength for $Eu^{3+}$ ions incorporated in a composite according to the present invention.
Figure 3B:
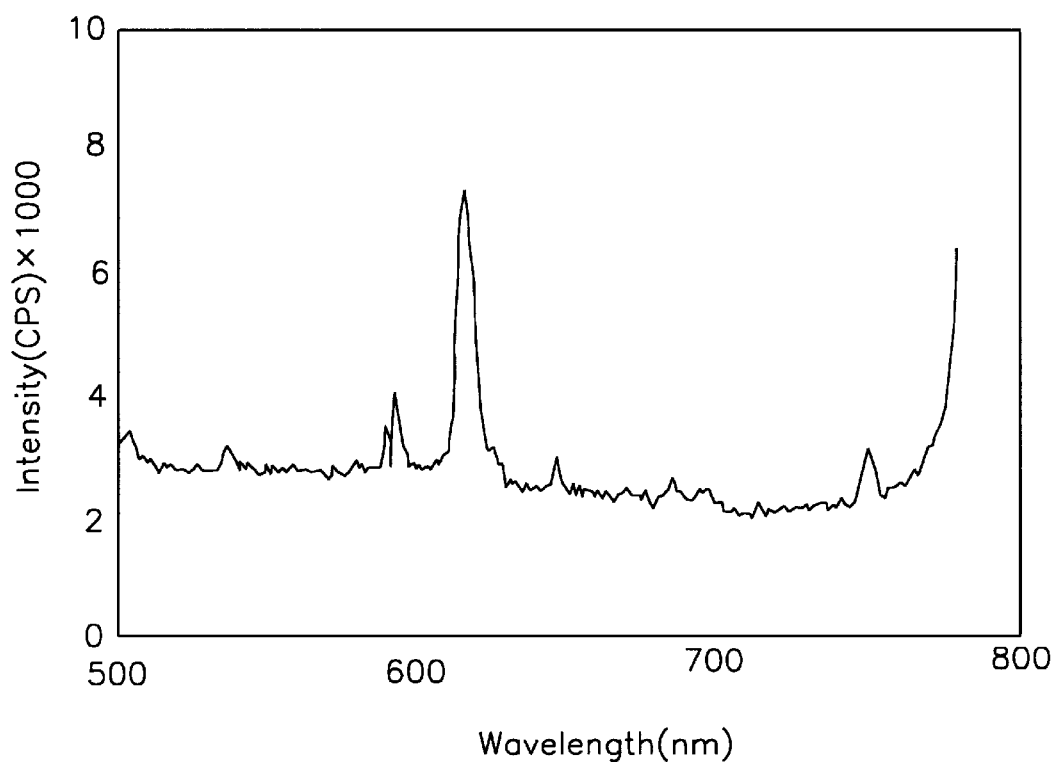
FIG. 3b is a luminescence-emission spectrum as a function of wavelength for $Eu^{3+}$ ions incorporated into a PMMA homopolymer.

FIG. 3a shows a luminescence-emission spectrum of $Eu^{3+}$, ions from a body of the plate produced by cutting and grinding the nano composite of fosterite-PMMA incorporating $Eu^{3+}$ ions. FIG. 3b shows the luminescence-emission spectrum of $Eu^{3+}$, ions from a body of the plate produced by cutting and grinding a PMMA body incorporating $Eu^3$ ions.

As shown in FIGS. 3a and 3b, when compared to a PMMA body having the same size as the composite of Example 2, it was revealed that the local structure around any $Eu^{3+}$ ions is partially formed by mixing PMMA with 8 weight % of the inorganic oxide lattice structure and, hence, $Eu^{3+}$ ions in the composite of Example 2 exhibit a spectrum entirely different from that of $Eu^{3+}$ ions in just the PMMA body. That is, when the guest material having an optical characteristic is added to the nano composite made according to the invention, the local chemical environment around the guest material may be optically altered.

Carrying out the polymerization of the organic monomer around and within the inorganic oxide lattice structure of the gel in-situ, the nano composite of an organic compound and an inorganic compound can be prepared by a relatively simple process, without requiring chemical bond formation between the organic constituents and the inorganic constituents. In addition, problems such as shrinkage, fracture and certain distortions of the alcogel that generally occur during the preparation of the composite can be solved. The inorganic component of the composite has a stable oxide structure, even when it contains a plurality of different metals or complex metals.

The composites made according to the present invention do not exhibit any phase separation phenomenon between the organic and the inorganic components and have good optical characteristics. The weight ratio of the inorganic oxide constituents to the total composite is on the order of 4 to 8%. Although the weight ratio thereof is low, the inorganic oxide lattice structure has a greater influence on the optical characteristics of the guest material. Furthermore, by controlling the chemical composition of the inorganic oxide lattice structure, the optical characteristics exhibited by the guest material added to the composite as the host material, may be easily controlled.

While the present invention has been described in detail with reference to the preferred embodiments, those skilled in the art will be able to appreciate that various modifications and substitutions can be made thereto without departing from the nature and scope of the present invention as set forth in the appended claims.

What is claimed is:

1. A method of preparing a composite of an organic and inorganic compound, comprising the steps of:

preparing a metal alkoxide by reacting at least one metal with an alcohol;

mixing the metal alkoxide with a silicon-containing compound to form a solution;

reacting the mixed solution of the metal alkoxide and the silicon-containing compound with a catalyst to produce an alcogel of a metal oxide or a complex metal oxide, the resulting alcogel having an inorganic lattice structure;

centrifuging the alcogel to separate impregnated alcohol from the alcogel to form a gel;

adding an organic monomer into the gel;

polymerizing the organic monomer added to the gel to form an organic polymer containing the inorganic lattice structure; and permitting the organic polymer to harden to thereby form the composite.

2. The method of claim 1 wherein the catalyst is selected from the group consisting of hydrogen peroxide, peroxide of magnesium, peroxide of sodium and peroxide of lithium.

3. The method of claim 1 further comprising the step of adding a functional guest material to the mixed solution of the metal alkoxide and silicon-containing compound.

4. The method of claim 1, further comprising distributing $Eu^{3+}$ ion over the composite.

5. The method of claim 4, wherein the $Eu^{3+}$ ion is evenly distributed over the composite.

6. The method of claim 1 wherein the metal for producing the metal alkoxide is at least one metal selected from the group consisting of magnesium, sodium and lithium.

7. The method of claim 1 wherein the silicon-containing compound is a silicon alkoxide selected from the group consisting of tetraethylorthosilicate and tetramethylorthosilicate.

8. The method of claim 1 wherein the organic monomer is at least one compound selected from the group consisting of methylmethacrylate and methacrylate, the compound having polymerizable double bonds.

9. The method of claim 1 wherein the centrifuging and polymerizing steps are carried out in a same reaction vessel.

10. The method of claim 1 wherein the polymerizing step is carried out such that the organic monomer forms polymer chains within and around the inorganic lattice structure in-situ.

11. The method of claim 1 wherein the organic polymer and the inorganic lattice are uniformly distributed in the composite.

12. The method of claim 1 wherein the gel having the inorganic lattice structure is dispersed throughout the organic monomer during the polymerization step.

13. The method of claim 1 further comprising, after centrifuging the alcogel, centrifuging the gel and adding additional amounts of the organic monomer to remove any remaining impregnated alcohol.

14. The method of claim 1 further comprising, after centrifuging the alcogel, centrifuging the gel and repeatedly adding additional amounts of the organic monomer to increase the amount of monomer flowing into the gel.

* * * * *